United States Patent [19]

Osaki

[11] Patent Number: 4,943,778

[45] Date of Patent: Jul. 24, 1990

[54] INSTRUMENT FOR MEASURING HIGH FREQUENCY CHARACTERISTICS OF SHEET-LIKE MATERIALS

[75] Inventor: Shigeyoshi Osaki, Takarazuka, Japan

[73] Assignee: Kanzaki Paper Manufacturing Co., Ltd., Japan

[21] Appl. No.: 287,442

[22] Filed: Dec. 20, 1988

[30] Foreign Application Priority Data

Dec. 21, 1987 [JP] Japan ................................. 324980

[51] Int. Cl.⁵ ........................................... G01N 22/00
[52] U.S. Cl. .................................. 324/636; 324/635; 324/641
[58] Field of Search ............... 324/58 R, 58 C, 58.5 C, 324/58.5 R, 58 A, 58.5 A

[56] References Cited

U.S. PATENT DOCUMENTS 3,458,808 7/1969 Agdur ............................ 324/58.5 C
4,781,063 11/1988 Osaki et al. ................. 324/58.5 C X

FOREIGN PATENT DOCUMENTS 667927 8/1963 Canada ........................... 324/58.5 C
0176889 4/1986 European Pat. Off. .......... 324/58 R
83946 of 1986 Japan .

OTHER PUBLICATIONS

Dube et al.; "Determination of Dielectric Properties . . . "; J. Appl. Phys., vol. 44, No. 11 (Nov. 1973), pp. 4927-4929.
Ahluwalia et al.; "Microwave Test Chamber . . . ", J. Microwave Power 6(1), (1971), pp. 15-23.
Hanfling et al.; "Measurement of Dielectric Materials . . . "; IEEE Trans. on Microwave Theory and Techniques, vol. MTT 20, No. 3, Mar. 1972, pp. 233-235.

Primary Examiner—Reinhard J. Eisenzopf
Assistant Examiner—Robert W. Mueller
Attorney, Agent, or Firm—Morgan & Finnegan

[57] ABSTRACT

An instrument for measuring the high frequency characteristics of a sheet-like material comprising: a pair of opposed slits formed in a pair of opposed tube walls of a cavity resonator having an optional cross-sectional shape, said slits extending parallel to the tube axis and enabling a sheet-like material to be inserted such that it extends across said cavity resonator; a driving section disposed at one end of said cavity resonator and having a driving conductor for producing microwaves for driving said cavity resonator in the direction to form an electric field which is perpendicular to the tube wall surfaces formed with said pair of slits; a detecting section disposed at the other end of said cavity resonator and having a probe conductor for receiving said microwaves; and a controlling and calculating device for detecting the resonant frequency or attenuation of received microwaves and calculating the high frequency characteristics of the sample from the detection result.

5 Claims, 2 Drawing Sheets

INSTRUMENT FOR MEASURING HIGH FREQUENCY CHARACTERISTICS OF SHEET-LIKE MATERIALS

TECHNICAL FIELD

The present invention relates to an instrument for measuring high frequency characteristics, such as dielectric constant, dielectric loss and attenuation of microwaves, of materials by utilizing microwaves.

PRIOR ART

A method of measuring the anisotropy of a sheet-like material by detecting the dielectric constant of the material is proposed in Japanese Patent Application No. 205,992 of 1984. This method comprises the steps of preparing a cavity resonator having a slit in the middle portion thereof extending across the cross-section, i.e., extending around the four walls which define the rectangular cross-section, inserting a microwave driving conductor in one end of the cavity resonator and a detection probe in the other end, thereby detecting the attenuation or resonant frequency of microwaves passing through the sample sheet. With this conventional construction, although the fiber orientation of paper or the like which produces a relatively high variation in dielectric characteristics can be measured with high accuracy, the molecular orientation of a thin film or the like which produces a faint variation in the characteristics cannot be measured with high accuracy. This problem stems from the fact that detection sensitivity is influenced as a function of the volume of a sample sheet which is a medium for propagation and transmission of microwaves, i.e., the cross-sectional area of a cavity resonator.

With the above in mind, the present invention has for its object the provision of an instrument for measuring the high frequency characteristics of a sheet-like material with high accuracy by improving the disposition of the sheet insertion slits in the conventional cavity resonator.

SUMMARY OF THE INVENTION

To achieve the above object, an instrument for measuring the high frequency characteristics of a sheet-like material comprises:

a pair of opposed slits formed in a pair of opposed tube walls of a cavity resonator having an optional cross-sectional shape, said slits extending parallel to the tube axis and enabling a sheet-like material to be inserted such that it extends across said cavity resonator;

a driving section disposed at one end of said cavity resonator and having a driving conductor for producing microwaves for driving said cavity resonator in the direction to form an electric field which is perpendicular to the tube wall surfaces formed with said pair of slits;

a detecting section disposed at the other end of said cavity resonator and having a probe conductor for receiving said microwaves; and a controlling and calculating device for detecting the resonant frequency or attenuation of received microwaves and calculating the high frequency characteristics of the sample from the detection result.

According to the above arrangement, since the slit length can be increased as compared with the conventional example, the area of the portion of a sheet-like material to be inserted in the cavity resonator can be increased, thereby making it possible to increase the difference in the amount of variation in the resonance frequency or attenuation before and after insertion of the materials; thus, the detection sensitivity can be increased.

DESCRIPTION OF THE PREFERRED EMBODIMENTS

Figure 1:
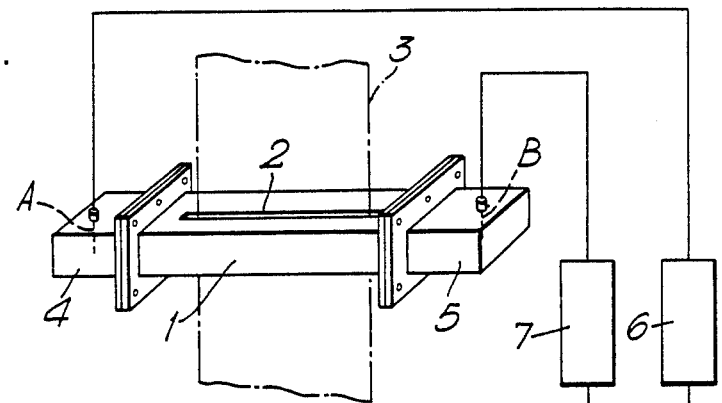
FIG. 1 is a schematic perspective view showing an embodiment of the present invention.

FIG. 1 shows an instrument according to an embodiment of the invention. A cavity resonator 1 is formed of a waveguide tube preferably having a rectangular cross-section. A pair of opposed slits 2 is formed centrally at the opposed longer tube walls of the resonator 1 (in the figure, only one of the two slits, the one formed in the upper tube wall, being shown) extending parallel to the tube axis, so that a sheet-like material 3 can be inserted in the slits 2. In addition, the cross-sectional shape of the cavity resonator 1 may be a quadrangle which is close to a square, or a cylinder. The cavity resonator 1 is provided at one end thereof with a driving section 4 and at the other end with a detecting section 5, said driving section 4 having a driving conductor or transmitting antenna A inserted therein to emit microwaves which drive the cavity resonator 1 to form an electric field which is perpendicular to the wall surfaces formed with the slits 2, said detecting section 5 having a detecting probe or receiving antenna B inserted therein. The driving and detecting sections 4 and 5, respectively, are connected to a sweep oscillator 6 and a detector 7 through respective coaxial cables, it being arranged that in the vicinity of the resonant frequency of the cavity resonator 1, the sweep oscillator 6 feeds a microwave drive current of variable frequency (for example, 4 GHz). In the cavity resonator 1, the slits 2 are positioned in the minimum electric field directed in the transverse direction which is perpendicular to the tube axis. Since essentially there is no displacement current across the slits 2, the presence of the slits 2 causes no trouble to resonance in the cavity. When a sheet material 3 is inserted in the slits 2, it follows that the sheet-like material lies in the path of propagation of microwaves. The dielectric characteristics of the sheet-like material 3 causes the resonant frequency to vary from the value when the sheet-like material is absent, said resonant frequency being detected as the frequency at the maximum output point from the relation between the sweep frequency and the detection output. In an arithmetic section 8, these values are converted to various characteristics which are then outputted to a suitable output device.

The system for detecting the attenuation of microwaves operates on the principle of fixing the driving frequency of the cavity resonator at a frequency which is slightly higher than the resonant frequency when no material is inserted in the cavity resonator (i.e., fixing the driving frequency at a frequency which is expected to be present as a resonant frequency when a material is inserted), measuring the intensity of transmitting microwaves before and after the insertion of the material in the cavity resonator, and causing the arithmetic section 8 to calculate the attenuation from the relation between the values obtained before and after said insertion of the material.

Figure 4:
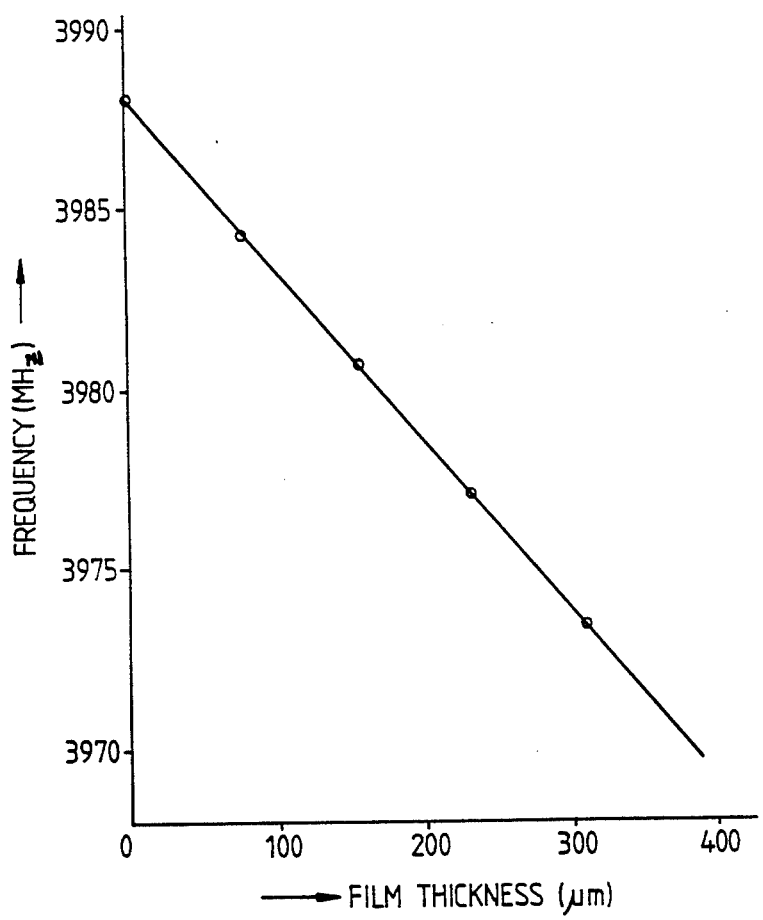
FIG. 4 is a graph showing a calibration curve of resonant frequency versus film thickness measured in accordance with the invention.

The present instrument can be used to detect the anisotropy of biaxially oriented films on the basis of the difference in biaxial dielectric characteristics and also to measure the thickness of synthetic resin films or the like. That is, if the dielectric constant of a film is measured in advance by one method or another, the thickness of the film can be measured from the relation between the variation in resonant frequency or the attenuation measured in the manner described above and the dielectric constant. FIG. 4 is a calibration curve obtained by successively stacking biaxially stretched polyethylene terephthalate films (78 μm thick and 40 mm wide webs) and measuring their relation to the resonant frequency, it being understood that a substantially perfectly proportional relation is obtained.

It is also applicable to the measurement of the composition ratio of copolymers or blends of two macromolecular materials. In this case, this can be measured by using a calibration curve which indicates the relation between the composition ratio of a material with a substantially constant thickness determined in advance and the resonant frequency or the intensity of transmitting microwaves and, if necessary, performing calculations for calibration.

Figure 2:
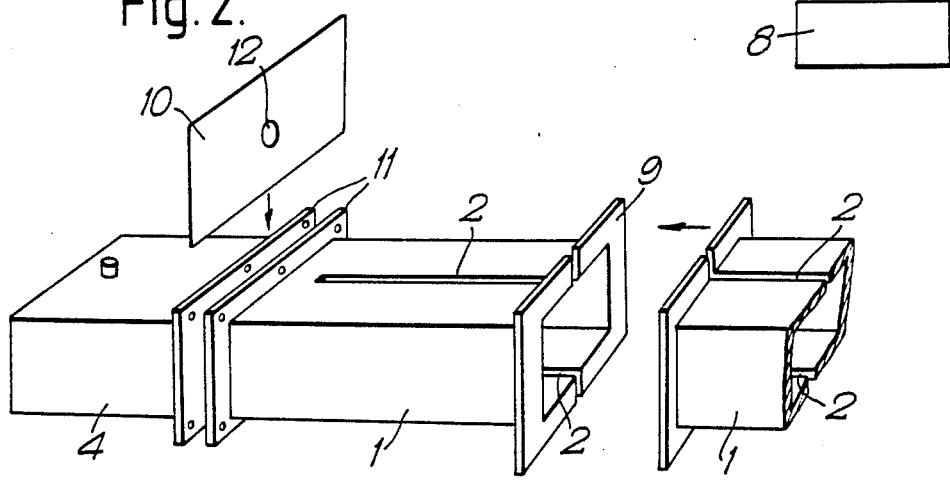
FIG. 2 is a principal perspective view of another embodiment of the invention.

FIG. 2 shows another embodiment of the invention using a cavity resonator adapted to be bisected at the central cross-section. More particularly, in the cavity resonator of FIG. 1, it is not easy to insert the sheet-like material 3 into the cavity resonator if the material is soft; thus, there is adopted a method of insertion which comprises the steps of sticking the leading end of the material and inserting it into the slits while thus maintaining it in the stiff state. However, in some cases, sticking it to a hard sheet is difficult depending upon the kind of the material, thus leaving the insertion still difficult. Accordingly, in the embodiment shown in FIG. 2, to facilitate the insertion of a material, the cavity section of the resonator 1 is bisected at the central cross-section and the slits 2 are made in the form of longitudinal grooves extending from flanges 9 at the divided ends. One half of the cavity section (e.g., the right-hand side) is separated axially of the tube from the other half to allow a sheet-like material to be inserted into the slits 2 along the latter from the flanged ends of these halves, thereby facilitating the insertion of the material into said slits. Further, in FIG. 2, the numeral 10 denotes a shielding plate to be inserted between flanges 11 formed at the boundary between the cavity section and the driving section 4 or detecting section 5. A hole 12 in the shielding plate establishes communication between the two sections, thereby increasing the Q of the cavity resonator 1 to compensate for a decrease in Q caused by the slits 2. In addition, it may be arranged that one half of the cavity section is slidable in a direction at right angles to the tube axis.

Examples of dimensions of the various parts of the present instrument and characteristics are shown below.

| | |
|---|---|
| Overall length of cavity resonator: | 203.0 mm (inside dimension) |
| *-continued* | |
| Cross-sectional dimensions of cavity section: | 29.1 mm × 58.1 mm |
| Dimensions of slits: | 1.0 × 40.0 mm |
| Central position of shielding wall: | 27.5 mm from end |
| Thickness of shielding plate: | 0.155 mm |
| Material of shielding plate: | silver-plated brass |
| Q value: | 1000 or higher |
| Oscillator: | cavity oscilator (300 MHz-30 GHz) |
| Sampling: | 1000 times/sec |

In addition, in this example, it is arranged that 1.5 wavelengths at the resonant frequency (4 GHz) enter the cavity (length: 148 mm); however, the number of wavelengths which is an integral multiple of half wavelength is acceptable.

MERITS OF THE INVENTION

Figure 3:
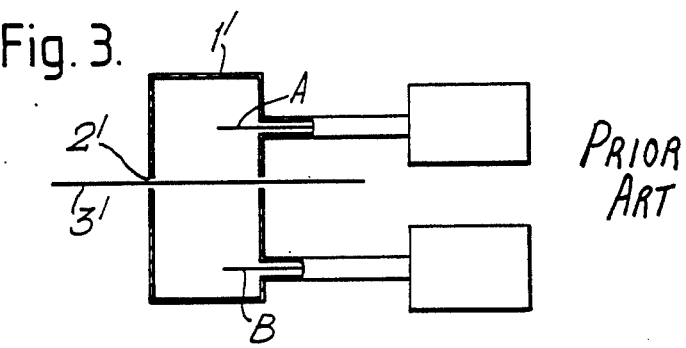
FIG. 3 is a schematic view of the construction of a conventional example.

As has been described so far, the instrument for measuring the dielectric characteristics of sheet-like materials according to the invention is designed to measure the dielectric characteristics of a sheet-like material by forming opposed slits in the central regions of the tube walls of a cavity resonator on the opposite long sides thereof, where slits extend parallel to the tube axis, and measuring the resonant frequency or attenuation of microwaves with a sample sheet inserted in the cavity. This construction makes it possible to increase the length of the slits as compared with conventional slits and increase the area of the portion of a material to be inserted in the cavity resonator, so that values of resonant frequency or attenuation found with and without the material inserted can be increased; thus, there is a merit that the anisotropy, thickness and composition ratio of thin films can be measured with high sensitivity In addition, in a cavity resonator of conventional construction for measuring sheet-characteristics shown in FIG. 3, if the cavity resonator 1 has the same dimensions as in the example of design in embodying the present invention shown above, the microwave-acted area of a sheet-like material 3' inserted into the slits 2' is equal to the cross-sectional area of the cavity of the resonator: 29.1 mm×58.1 mm. In the present invention, however, it is 29.1 mm (cavity thickness)×132.0 mm (slit length), it being obvious that even a 1.5-wavelength construction provides a value which is twice or higher in an area.

What is claimed is:

1. An instrument for measuring the high frequency characteristics of a sheet-like material comprising:
   a pair of opposed slits formed in a pair of opposed tube walls of a cavity resonator having an optional cross-sectional shape, said slits extending parallel to a longitudinal tube axis and enabling a sheet-like material to be inserted such that it extends across said cavity resonator;
   a driving section disposed at one end of said cavity resonator and having a driving conductor for producing microwaves for driving said cavity resonator to form an electric field which is perpendicular to the tube wall surfaces formed with said pair of slits;
   a detecting section disposed at the other end of said cavity resonator and having a probe conductor for receiving said microwaves;
   a controlling and calculating device for detecting the resonant frequency or attenuation of received microwaves and calculating the high frequency characteristics of the sample from the detection result; and wherein the cavity section of said cavity resonator is bisected at a halfway cross-section into two subsections, said slits are made in the form of longitudinal grooves extending from said subsections' bisected ends, and said subsections can be separated axially one from the other.

2. An instrument for measuring the high frequency characteristics of sheet-like materials including:
    a cavity resonator made of a tubular structure, said cavity resonator bisected at a halfway cross-section into two subsections, said subsections being separable away axially one from the other;
    a pair of opposed slits formed in a pair of opposed tubular walls of said cavity resonator, each said slit cut into one of said subsections beginning at said halfway cross-section, said slits extending parallel to the longitudinal direction of the tubular structure and enabling a sheet-like material to be inserted such that it extends across said cavity resonator;
    a driving section disposed at one end of said cavity resonator and having a driving conductor for producing microwaves for driving said cavity resonator to form an electric field which is perpendicular to the tubular wall surfaces formed with said pair of slits;
    a detecting section disposed at the other end of said cavity resonator and having a probe conductor for receiving said microwaves; and
    a controlling and calculating device for detecting the resonant frequency or attenuation of received microwaves and calculating the high frequency characteristics of the sample from the detection result.

3. An instrument as recited in claim 2, further including at least one shielding plate interposed between said cavity resonator and at least one of said driving and detecting sections, said shielding plate having a hole allowing microwave-communication between said cavity resonator and said driving and detecting section.

4. An instrument as recited in claim 2, wherein said cavity resonator is a wave guide tube having a rectangular cross-section.

5. An instrument for measuring the high frequency characteristics of a sheet-like material comprising:
    a cavity resonator made of a tubular structure having a rectangular cross-section, and bisected at a halfway cross-section into two subsections, said subsections being separable away axially one from the other;
    a pair of opposed slits formed in a pair of opposed tubular walls of said cavity resonator, each said slit extending across one of said two subsections in the form of a longitudinal groove from said halfway cross-section, and said slits extending parallel to a longitudinal direction of the tubular structure and enabling a sheet-like material to be inserted such that it extends across said cavity resonator;
    a driving section disposed at one end of said cavity resonator and having a driving conductor for producing microwaves for driving said cavity resonator to form an electric field which is perpendicular to the tubular wall surfaces formed with said pair of slits;
    a detecting section disposed at the other end of said cavity resonator and having a probe conductor for receiving said microwaves;
    at least one shielding plate interposed between said cavity resonator and at least one of said driving and detecting sections, said shielding plate having a hole through which a microwave-communication between said cavity resonator and said driving and detecting section; and
    a controlling and calculating device for detecting the resonant frequency or attenuation of received microwaves and calculating the high frequency characteristics of the sample from the detection result.

* * * * *

UNITED STATES PATENT AND TRADEMARK OFFICE
CERTIFICATE OF CORRECTION

PATENT NO. : 4,943,778

DATED : July 24, 1990

INVENTOR(S) : Shigeyoshi Osaki

It is certified that error appears in the above-identified patent and that said Letters Patent is hereby corrected as shown below:

In Col. 2, line 35, "A" should read -- $\underline{A}$ --; on line 39, "3" should read -- $\underline{B}$ --.

In Col. 4, line 36, a period (.) should be inserted after -- sensitivity --; on line 39, "1" should read -- 1' --.

Signed and Sealed this

Twelfth Day of May, 1992

Attest:

DOUGLAS B. COMER

Attesting Officer

Acting Commissioner of Patents and Trademarks